US008678007B2

(12) United States Patent
Porter, III (10) Patent No.: US 8,678,007 B2
(45) Date of Patent: Mar. 25, 2014

(54) PATIENT SUPPORT SYSTEM AND METHOD (76) Inventor: Winston Allen Porter, III, Atlanta, GA (US)

( * ) Notice: Subject to any disclaimer, the term of this patent is extended or adjusted under 35 U.S.C. 154(b) by 57 days.

(21) Appl. No.: 13/038,457

(22) Filed: Mar. 2, 2011

(65) Prior Publication Data

US 2011/0213503 A1 Sep. 1, 2011

Related U.S. Application Data (63) Continuation-in-part of application No. 12/435,000, filed on May 4, 2009.

(60) Provisional application No. 61/104,578, filed on Oct. 10, 2008.

(51) Int. Cl.
*A61G 15/00* (2006.01)
*A47C 27/08* (2006.01)

(52) U.S. Cl.
USPC ......... 128/845; 5/600; 5/615; 5/652; 5/655.3; 5/706

(58) Field of Classification Search
USPC .......... 128/845; 5/86.1, 600, 615, 652, 655.3, 5/690, 706, 707, 710, 711, 713, 945; 297/DIG. 4
See application file for complete search history.

(56) References Cited

U.S. PATENT DOCUMENTS

| 5,044,029 | A | 9/1991 | Vrzalik |
| 5,051,673 | A | 9/1991 | Goodwin |
| 5,062,171 | A | 11/1991 | Vrzalik |
| 5,152,021 | A | 10/1992 | Vrzalik |
| 5,235,713 | A | 8/1993 | Guthrie et al. |
| 5,652,985 | A | 8/1997 | Wilkinson et al. |

(Continued)

FOREIGN PATENT DOCUMENTS

| EP | 1 400 228 | 3/2004 |
| JP | 64-027558 | 1/1989 |

(Continued)

OTHER PUBLICATIONS

Non Final Office Action issued Oct. 12, 2011 for U.S. Appl. No. 12/435,000.

(Continued)

*Primary Examiner* — Patricia Bianco
*Assistant Examiner* — Keri J Nelson
(74) *Attorney, Agent, or Firm* — Ballard Spahr LLP (57) ABSTRACT

A patient support system for a wheelchair is provided. At least a portion of the patient support system components form a no-air-loss patient support surface. At least one fluid pump can supply air pressure to a plurality of no-air-loss air cells, and at least one pressure release valve can release air pressure from the no-air-loss air cells. A computer can compare air pressure within the air cells to a desired air pressure set point and can modulate the air pressure by actuating the at least one fluid pump and/or the at least one pressure release valve to bring the air pressure within the air cells to a desired air pressure. After the initial air pressure adjustments are made and the desired air pressure is achieved, no further adjustments during the operation are able to be made by the computer so that the patient positioned thereon the patient support system will not be moved by the patient support system during an operation.

27 Claims, 9 Drawing Sheets

(56) References Cited

U.S. PATENT DOCUMENTS

| | | | |
|---|---|---|---|
| 5,815,864 A | 10/1998 | Sloop | |
| 5,848,450 A | 12/1998 | Oexman et al. | |
| 5,963,997 A | 10/1999 | Hagopian | |
| 6,073,284 A | 6/2000 | Borders | |
| 6,115,860 A | 9/2000 | Vrzalik | |
| 6,148,461 A | 11/2000 | Cook et al. | |
| 6,560,804 B2 | 5/2003 | Wise et al. | |
| 6,709,246 B2 * | 3/2004 | Boyd | 417/423.1 |
| 7,039,972 B2 | 5/2006 | Chaffee | |
| 7,246,856 B2 * | 7/2007 | Kruse et al. | 297/330 |
| 7,287,289 B1 | 10/2007 | Hagopian | |
| 2003/0200611 A1 | 10/2003 | Chaffee | |
| 2005/0091752 A1 | 5/2005 | Gowda | |
| 2006/0179579 A1 | 8/2006 | Phillips et al. | |
| 2008/0010748 A1 | 1/2008 | Menkedick et al. | |

FOREIGN PATENT DOCUMENTS

| | | |
|---|---|---|
| WO | WO 99/18827 | 4/1999 |
| WO | WO 01/62198 | 8/2001 |
| WO | WO 2006/089050 | 8/2006 |

OTHER PUBLICATIONS

International Search Report and Written Opinion for International Application No. PCT/US2009/060046 (mailed Apr. 29, 2010).

* cited by examiner

PATIENT SUPPORT SYSTEM AND METHOD

CROSS-REFERENCE TO RELATED APPLICATIONS

This application is a continuation-in-part application of U.S. Utility application Ser. No. 12/435,000, filed May 4, 2009, which claims the benefit of U.S. Provisional Application No. 61/104,578, filed on Oct. 10, 2008.

FIELD OF THE INVENTION

The field of this invention relates generally to seats used for supporting a patient for an extended period of time, such as a wheelchair, and more particularly to a patient support system for a wheelchair for the reduction or prevention of decubitus ulcers, more commonly known as "bedsores."

BACKGROUND OF THE INVENTION

Bedsores are lesions on the body that can be caused by factors including friction and shearing forces, however the most common cause of bedsores is unrelieved pressure. In most cases, this unrelieved pressure occurs when a patient remains in a stationary position for a period of time, for example, on an operating room table during a surgical procedure, and pressure from the weight of the body compresses tissue. Similarly, patients who are unable to move their legs and sit in a wheelchair for a prolonged period of time experience a continuous tissue compression under their ischial tuberosity. This compression of tissue over time leads to decrease of vascular flow, hypoxia, and/or ischemia and eventually to tissue necrosis (tissue death) if left untreated. This injury starts at the point of highest compression between tissue and bone, working its way to the skin surface and the appearance of a bedsore.

Low-air-loss patient support systems have been successful in reducing the occurrence of bedsores. However, these support systems continually leak air and therefore, unless air is added to the system, the air pressure within the low-air-loss patient support system continually decreases as the system deflates. Static readjusting low-air-loss patient support systems and/or low-air-loss patient support systems must continually be monitored so that the when the air pressure within the system has dropped below a desired set point air pressure, a pressure-raising means can be activated to increase the air pressure within the low-air-loss patient support system. Thus the pressure-raising means, typically a fluid pump, is cycled on and off, which changes the relative position of the patient with respect to the surface as the air pressure within the low-air-loss patient support system is continually changing. A pressure measuring device and pressure raising means, such as the fluid pump, must be carried with the low-air-loss patient support system to readjust the support system to the desired set point air pressure, thereby adding a cumbersome object and undue weight to, for example, a wheelchair.

Additionally, the pressure raising means is typically powered by a battery. In the event of battery depletion or failure, patients risk pressure support failure should the battery deplete or fail while the patient is on the mobile device.

Additionally, conventional wheelchair pressure relief devices either require the patient to load a control unit from a support bed or purchase an additional unit to calibrate the wheelchair support system. In view of the preceding, there is a need for a patient support system for a wheelchair for the reduction or prevention of bedsores.

SUMMARY

This application relates to a patient support system for a wheelchair. In one aspect, the patient support system can comprise a plurality of air cells, a control system, and an air supply system, which can exemplarily comprise at least one of: at least one fluid pump, at least one pressure release valve, and a plurality of tubing. In another aspect, the plurality of air cells can be configured to rest on or otherwise engage the wheelchair, so that a patient is supported by the patient support system in a manner to reduce or eliminate bedsores.

The wheelchair can be a conventional wheelchair as commonly known in the arts, comprising a support surface. In one aspect, the support surface can comprise a plurality of surface segments that can vary in size. It will be appreciated that the patient support system can be dimensioned or formed in different sizes as well so that the patient support system can be used with a variety of wheelchair types and models.

The plurality of air cells, in one aspect, can be elongate air cells, each having a proximal end and a distal end. In another aspect, the elongate air cells can have a length approximately equal to the width of the support surface of the wheelchair. In still another aspect, the plurality of air cells can be spaced from each other and arranged substantially parallel to each other. In another aspect, the plurality of air cells can be securely attached to at least one mounting sheet to substantially fix the location and orientation of the plurality of air cells. In yet another aspect, each air cell can have a single opening that places the air cell in sealed fluid communication with the air supply system, thus allowing air to flow into and/or out of each air cell. In another aspect, the opening of each air cell can be located at either the proximal end or the distal end of any of the plurality of air cells. It is also contemplated that the opening of each air cell can be located at any desired position on the respective air cells. In still another aspect, at least one liquid-impermeable covering can be configured to cover the plurality of air cells and/or the at least one mounting sheet. In still another aspect, at least one foam pad can be configured to provide a backup support system underneath the plurality of air cells. When assembled as part of the patient support system, because there is no venting means located within any air cells of the plurality of air cells, the plurality of air cells can be pressurized and sealed so that at least a portion of the plurality of air cells form a no-air-loss patient support surface.

In one aspect, the at least one fluid pump can be in fluid communication with the plurality of air cells, providing pressurized air therethrough the tubing to the plurality of air cells. Optionally, the at least one fluid pump can comprise two fluid pumps, three fluid pumps, or any number of fluid pumps, as desired. In one aspect, if a plurality of fluid pumps are present, the plurality of fluid pumps can be in communication with the plurality of tubing and each other by, for example and without limitation, a parallel or a series communication arrangement. However, in another aspect, the fluid pumps can form a plurality of air supply subsystems wherein the plurality of fluid pumps are not in communication with each other. In this aspect, a first fluid pump can supply air to a first air cell or first plurality of air cells, a second fluid pump can supply air to a second air cell or second plurality of air cells and so on, for each fluid pump provided in the air supply system.

In another aspect, at least one pressure release valve can be in sealed fluid communication with the plurality of air cells. In one aspect, the at least one pressure release valve can release air from the plurality of air cells and/or the plurality of tubing so that the air pressure within the patient support system can be can be maintained at a desired set point to reduce or prevent the formation of bedsores in a user of the system. Optionally, if a plurality of fluid pumps are arranged to form a plurality of air supply subsystems, a pressure release valve can be used to maintain the air pressure within each air supply subsystem at a desired set point.

The plurality of tubing can interconnect the at least one fluid pump, the at least one pressure release valve, the plurality of air cells, and the at least one pressure sensor, placing them in sealed fluid communication with each other, according to one aspect. In another aspect, the plurality of tubing can be configured to form at least one air cell manifold to more evenly distribute air to the plurality of air cells. In yet another aspect, the at least one air cell manifold can be attached to an at least one mounting sheet, formed integrally with the at least one mounting sheet, or can be unattached to the at least one mounting sheet.

The control system can comprise a computer and at least one pressure sensor that is configured to measure the pressure of a gas. The at least one pressure sensor can be operatively coupled, for example and without limitation, electrically, to the computer. In yet another aspect, the at least one pressure sensor can be in sealed fluid communication with the tubing and/or the plurality of air cells, so that the at least one pressure sensor can measure the air pressure within the air supply system or subsystems and can send a signal to the computer representing the measured air pressure.

In use, the computer can be operatively coupled, for example and without limitation, electrically, to the at least one pump, the at least one pressure release valve, and the at least one pressure sensor. In one aspect, the plurality of tubing can interconnect the at least one pump, the at least one pressure release valve, the at least one pressure sensor, and the plurality of air cells. In a further aspect, these components can be arranged to form a plurality of air supply subsystems, if desired, so that different air cells can be maintained at different desired air pressures.

In one exemplary aspect, at least a portion of the air cells of the patient support system can be placed onto a wheelchair. A user can input the desired patient support system air pressure set point into the computer and the at least one pressure sensor can send a signal to a processor of the computer representing the air pressure within the respective air cells. The processor can compare the signal from the at least one pressure sensor to the desired air pressure set point. If the sensed pressure is higher than the air pressure set point, the processor can send a signal to the appropriate at least one pressure release valve causing the valve to selectively open for a period of time, thus releasing air and decreasing the air pressure within the respective air cells. Conversely, if the sensed pressure is lower than the air pressure set point, the processor can send an actuation signal to the at least one fluid pump, thereby supplying additional air to the air cells and increasing air pressure within the air cells.

After a patient is positioned onto the no-air-loss patient support surface of the patient support system, the air pressure within the patient support system can change due to the weight of the patient. The at least one pressure sensor can detect this change, and the patient support system can adjust itself accordingly until the desired air pressure set point has been achieved. In one aspect, once the desired air pressure set point has been achieved, within a predetermined tolerance, no more adjustments to the air pressure within the patient support system are made. Because the plurality of air cells are no-air-loss air cells, air will not need to be added to the patient support system and the patient will not move or be moved during the operation due to system adjustments.

In one aspect, the pressure controlling device can be attached to a low-air-loss and/or a no-air-loss bed. The user can selectively switch the pressure controlling device to operate a no-air-loss wheelchair pad or a low or no-air-loss bed mattress. In one aspect, in use, when the air pressure within at least a portion of the plurality no-air-loss air cells is within a predetermined tolerance of the desired patient support system air pressure, the computer can signal the user that the system is at the desired pressure and ready to unhook from the pressure controlling device.

DETAILED DESCRIPTION OF THE FIGURES

These and other features of the preferred embodiments of the invention will become more apparent in the detailed description in which reference is made to the appended drawings wherein.

DETAILED DESCRIPTION OF THE INVENTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a device" can include two or more such devices unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

For clarity and conciseness, as used herein, the term "air" includes reference to air and/or any other fluid or combination of fluids. Thus, the plurality of air cells of the current application could comprise, for example, a plurality of water cells, nitrogen cells, and the like.

A patient support system 20 for a wheelchair 10 is provided, according to various aspects. In one aspect, as illustrated in FIGS. 2-9, the patient support system can comprise a plurality of air cells 30, an air supply system 40 and a control system 100. In another aspect, the plurality of air cells can be arranged to form a wheelchair pad 140 or a bed mattress. In another aspect, the air supply system can exemplarily comprise at least one of: at least one fluid pump 50, at least one pressure release valve 60, and a plurality of tubing 70 interconnecting the at least one fluid pump, the at least one pressure release valve, the plurality of air cells, and at least one pressure sensor.

Figure 1:
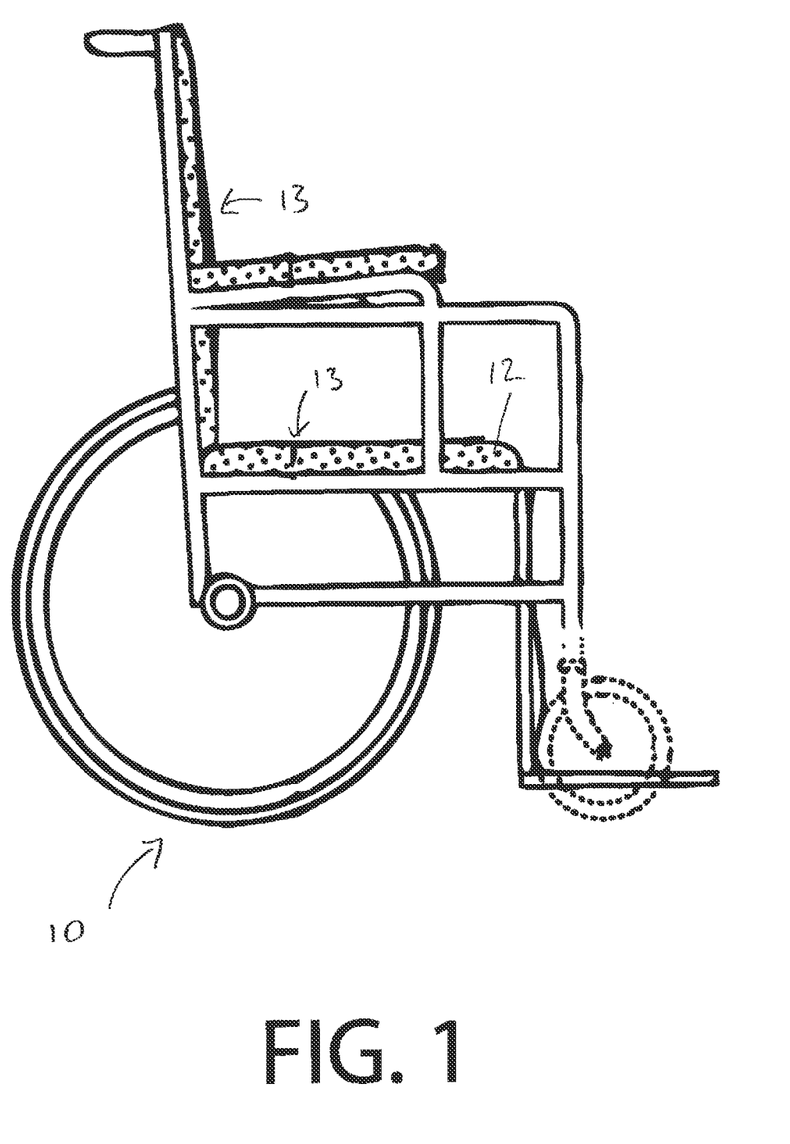
FIG. 1 is a perspective view of a conventional wheelchair.

The wheelchair 10 can be a conventional wheelchair as commonly known in the art and as exemplarily illustrated in FIG. 1. In one aspect, the wheelchair can comprise a support surface 12 for supporting at least a portion of a patient. In another aspect, the support surface can comprise a plurality of surface segments 13 for supporting a patient. In still another aspect, the plurality of surface segments can be arranged in various positions on the wheelchair to support the patient. The size of the support surface and the surface segments can vary depending on the type and model of wheelchair 10, again as commonly known in the art. The patient support system 20 can be dimensioned or formed in different sizes as well, as will be described more fully below, so that the patient support system can be used with a variety of wheelchair types and models. Optionally, it is contemplated that at least a portion of the patient support system can be integrated therein portions of the wheelchair.

Figure 2:
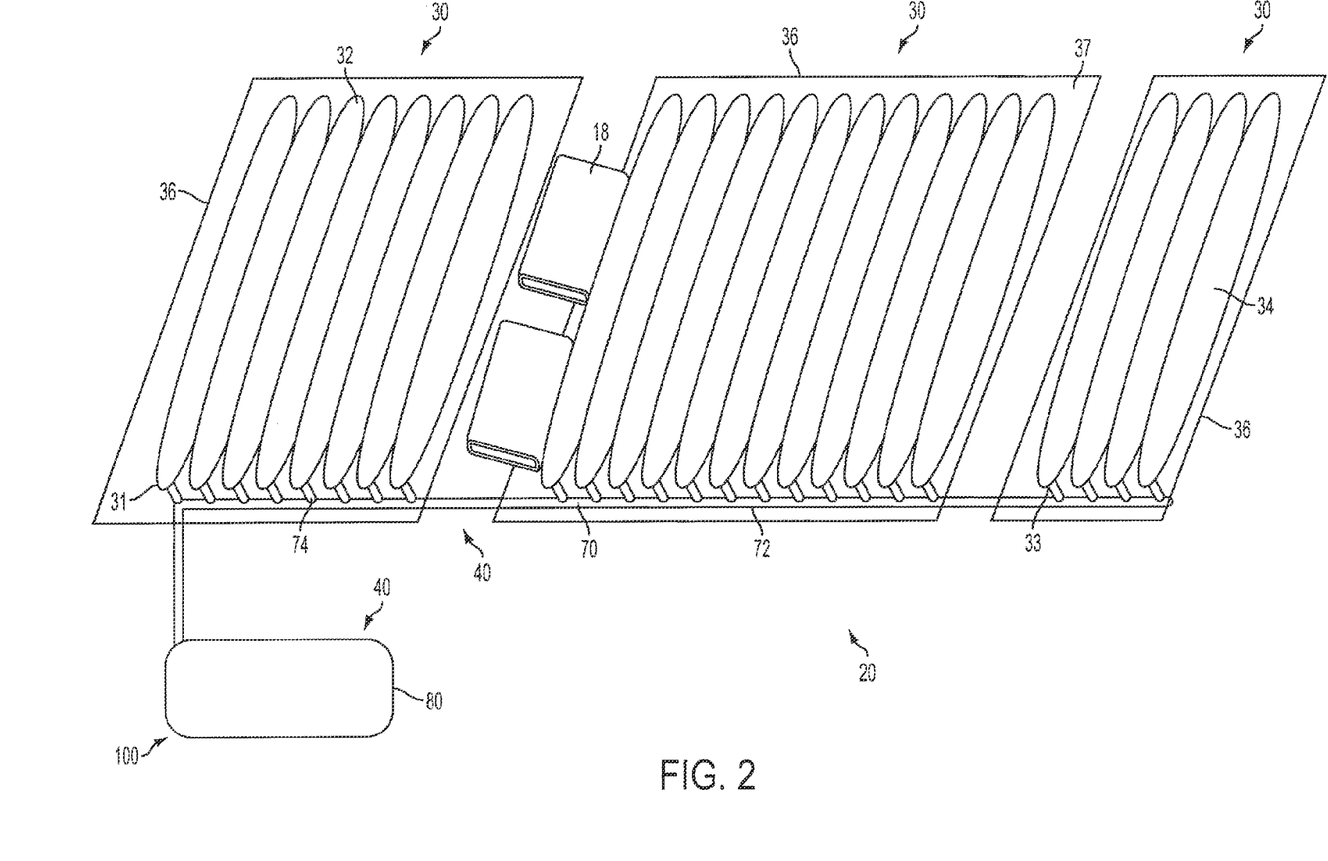
FIG. 2 is a schematic view of one embodiment of a patient support system, according to one aspect.
Figure 3:
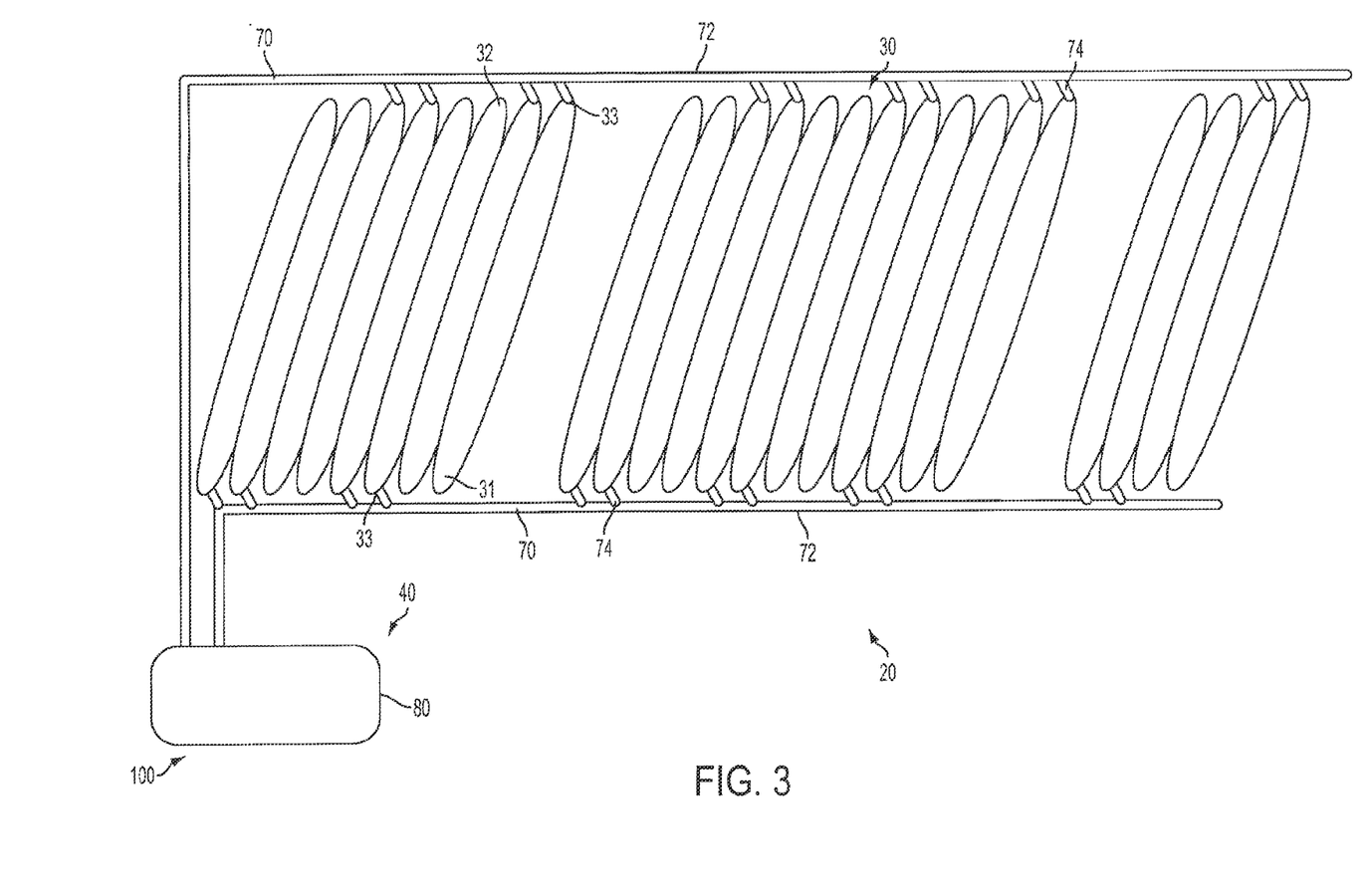
FIG. 3 is a schematic view of one embodiment of a patient support system, according to another aspect.
Figure 8:
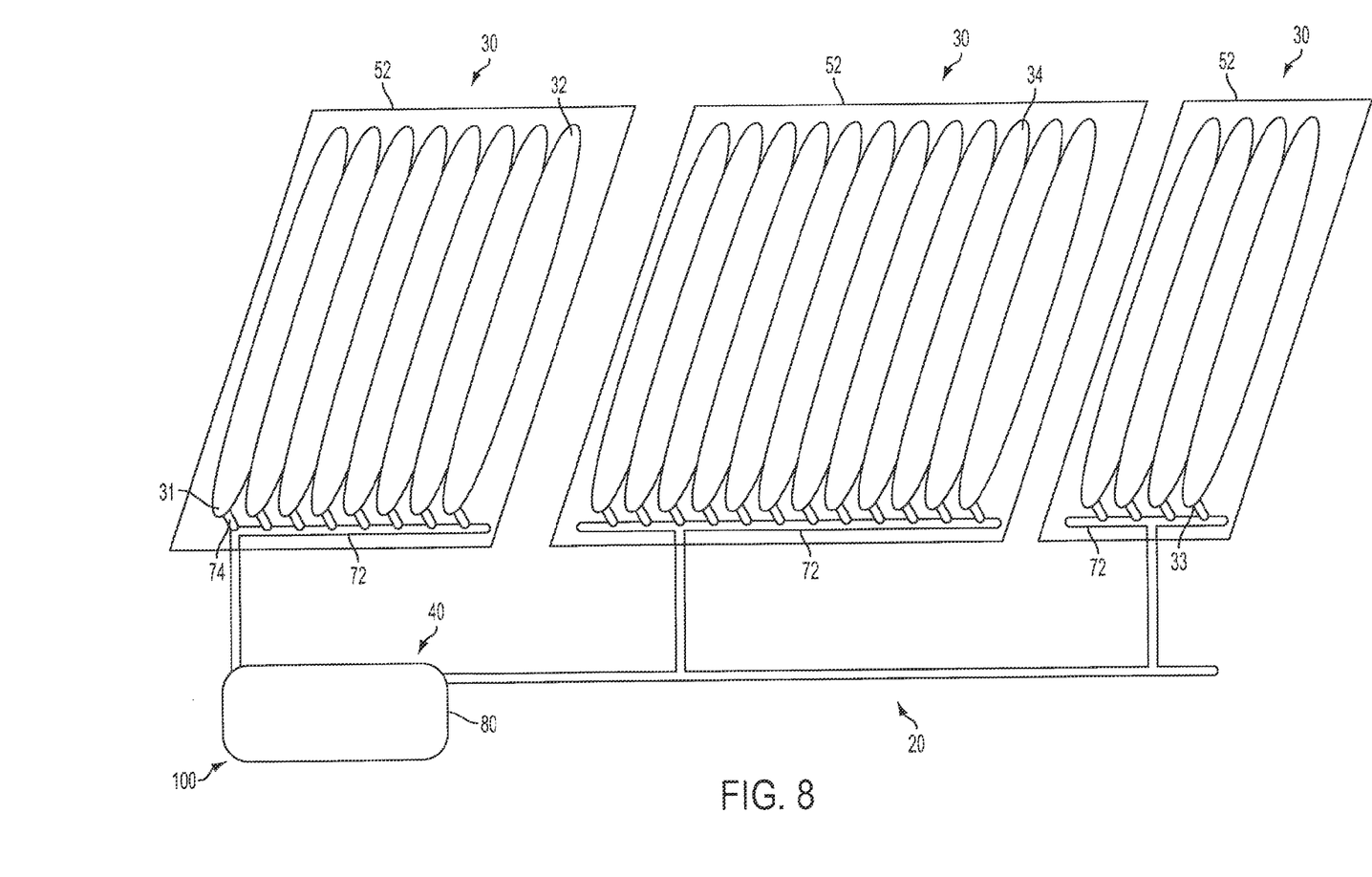
FIG. 8 is a schematic view of the patient support system of FIG. 2, according to one aspect, showing a plurality of air supply subsystems.

Each air cell of the plurality of air cells 30 can be an elongate air cell having a proximal end 31 and a distal end 32, as illustrated in FIGS. 2, 3 and 8. In one aspect, the plurality of air cells can be formed from a material that is not permeable. In another aspect, the plurality of air cells can be formed from an impermeable polymeric material, such as for example and without limitation, polyvinyl chloride. In another aspect, the elongate air cells can have a length approximately equal to the width of the support surface 12 or the plurality of surface segments 13 of the wheelchair 10. In another aspect, the plurality of air cells can be configured to rest on or otherwise engage the wheelchair. In still another aspect, the plurality of air cells can be spaced from each other and/or arranged substantially parallel to each other. In another aspect, each air cell can have an opening 33 in fluid communication with the air supply system 40, to allow air to flow into and/or out of each air cell. In one aspect, the opening of each air cell can be located at the proximal end 31 of the air cell. In another aspect, the opening of each air cell can be located at the distal end 32 of the air cell. In still another aspect, the opening 33 of each air cell can be located at the proximal end or the distal end of the air cell 30. In this aspect, it is contemplated that the location of the opening can alternate between the proximal end 31 of one air cell, the distal end 32 of the adjacent air cell, and so on. It is also contemplated that the location of the opening 33 of each air cell can be arranged in any combination of the proximal and distal ends of the air cells. Further, it is contemplated the openings 33 therein the respective air cells can be positioned as desired and are not limited to being positioned on respective proximal or distal end portions. In another aspect, the plurality of air cells can be no-air-loss air cells, because they have no other outlet (other than opening 33) for the air with which they are inflated to escape. Thus, in this aspect, each air cell of the plurality of air cells 30 has no venting means, such that air cannot enter or exit the interior of each air cell other than through the opening 33 in fluid communication with the air supply system.

Referring now to FIG. 3, an exemplary embodiment is shown in which a first pair of adjacent air cells having their openings located on their proximal end, is positioned adjacent a second pair of air cells having their openings located on their distal end. In this aspect, it is contemplated that the illustrated staggered relationship is continued. When assembled as part of the patient support system 20, as will be described more fully below, the plurality of air cells can be inflated so that at least a portion of the plurality of air cells form a no-air-loss patient support surface 34.

In another aspect, the plurality of air cells 30 can be securely attached to at least one mounting sheet 36 to substantially fix the location and orientation of the plurality of air cells relative to the at least one mounting sheet. In one aspect, the at least one mounting sheet can be a polymeric material dimensioned and sized such that the area of a top surface 37 of the mounting sheet is larger than then area of the plurality of air cells. In another aspect, the at least one mounting sheet 36 can comprise a plurality of mounting sheets dimensioned and sized to approximately fit thereon the support surface 12 or the plurality of surface segments 13 of the wheelchair 10. In another aspect, the at least one mounting sheet can be formed from the same material as the plurality of air cells 30. In a further aspect, the plurality of air cells can be conventionally affixed to the at least one mounting sheet 36 with, for example and without limitation, an adhesive. In another aspect, however, at least a portion of at least one of the plurality of air cells can be formed integrally with the at least one mounting sheet, such that at least a portion of an air cell is formed from at least a portion of the at least one mounting sheet.

In another aspect, the plurality of air cells can be positioned adjacent to each other by conventional methods, such as, for example and without limitation, adhesives, hook and loop fasteners, a container such as a mounting bag, and the like.

In one aspect, at least one liquid-impermeable covering can be configured to cover the plurality of air cells 30 and/or the at least one mounting sheet 36. It is contemplated that the liquid-impermeable covering can be made from polymeric components, such as, for example and without limitation, nylon or nylon coated with polyurethane. In yet another aspect, if a plurality of mounting sheets are present, a separate liquid-impermeable covering can be configured to cover each mounting sheet and the plurality of air cells 30 attached thereto. Thus, in this embodiment, for example, if three mounting sheets are provided, there can be three liquid impermeable coverings.

Figure 4:
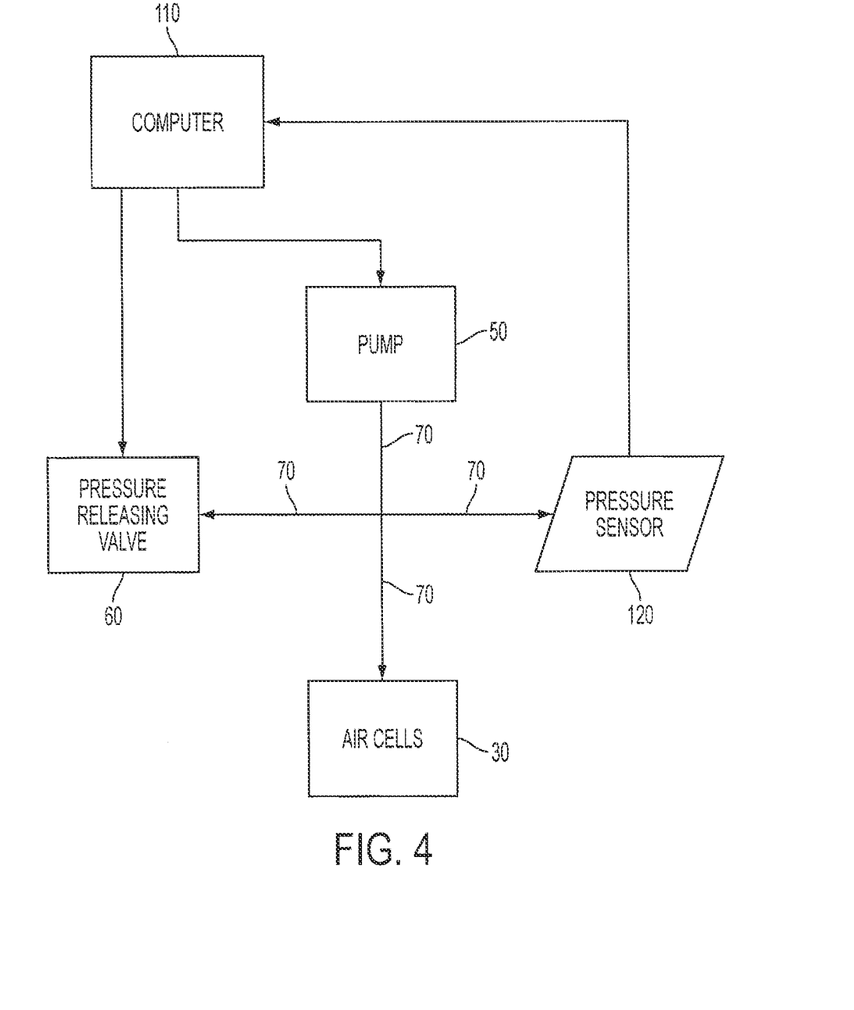
FIG. 4 is a schematic flow chart of one embodiment of the patient support system of the current application comprising one fluid pump.

One exemplary embodiment of the air supply system 40 is schematically illustrated in FIG. 4. In one aspect, the at least one fluid pump 50 can be a conventional fluid pump that is configured to provide the patient support system 20 with air at a desired pressure. The at least one fluid pump can be positioned in sealed fluid communication with the plurality of air cells 30 through the plurality of tubing 70. Optionally, it is contemplated that the at least one fluid pump can comprise two fluid pumps, three fluid pumps, or any number of fluid pumps as desired. In one aspect, the plurality of fluid pumps 50 can be in communication with the plurality of tubing 70 and each other by, for example and without limitation, a parallel communication arrangement, as exemplarily illustrated in FIG. 5.

Figure 6:
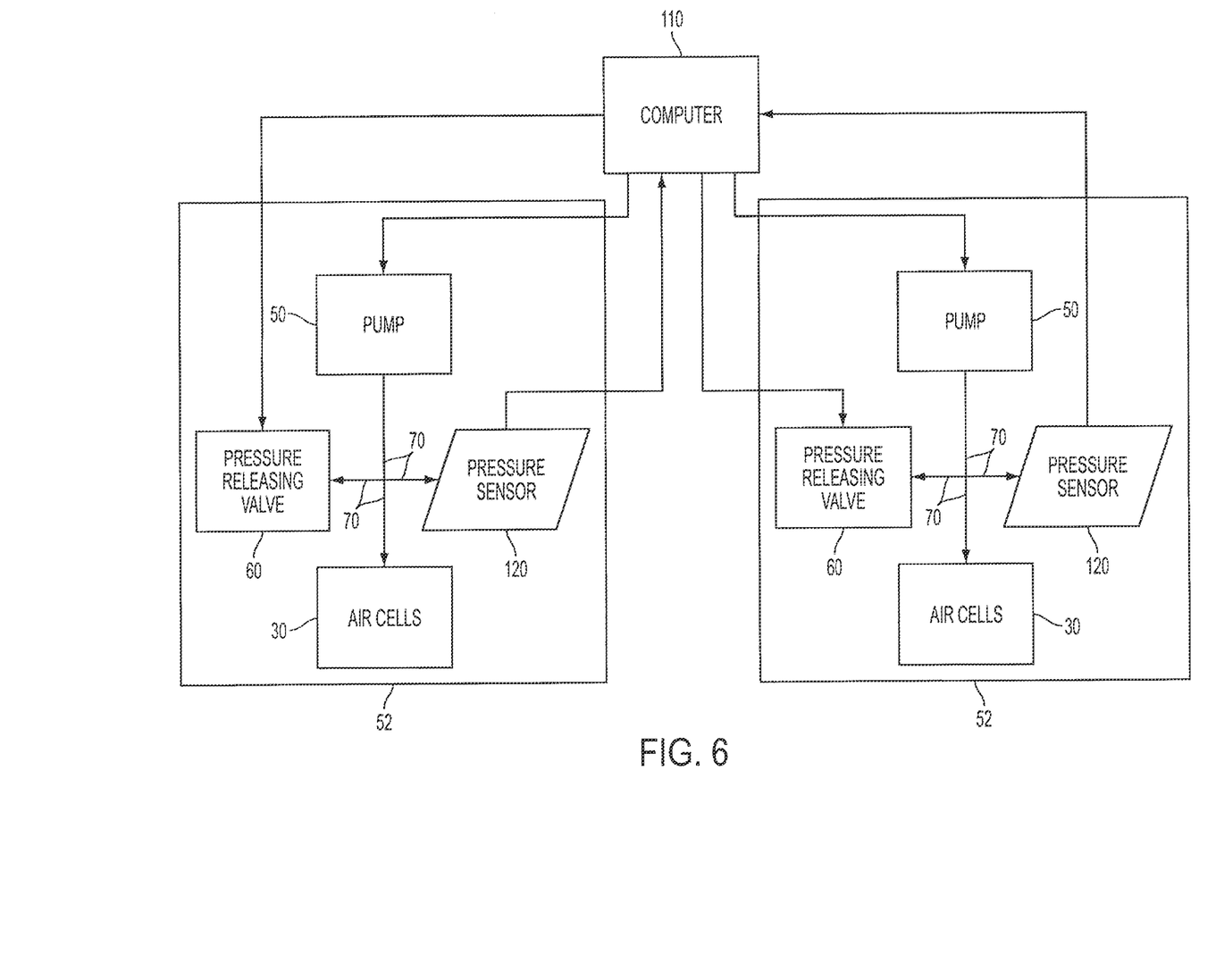
FIG. 6 is a schematic flow chart of one embodiment of the patient support system of the current application comprising a plurality of fluid pumps arranged to form a plurality of air supply subsystems.
Figure 7:
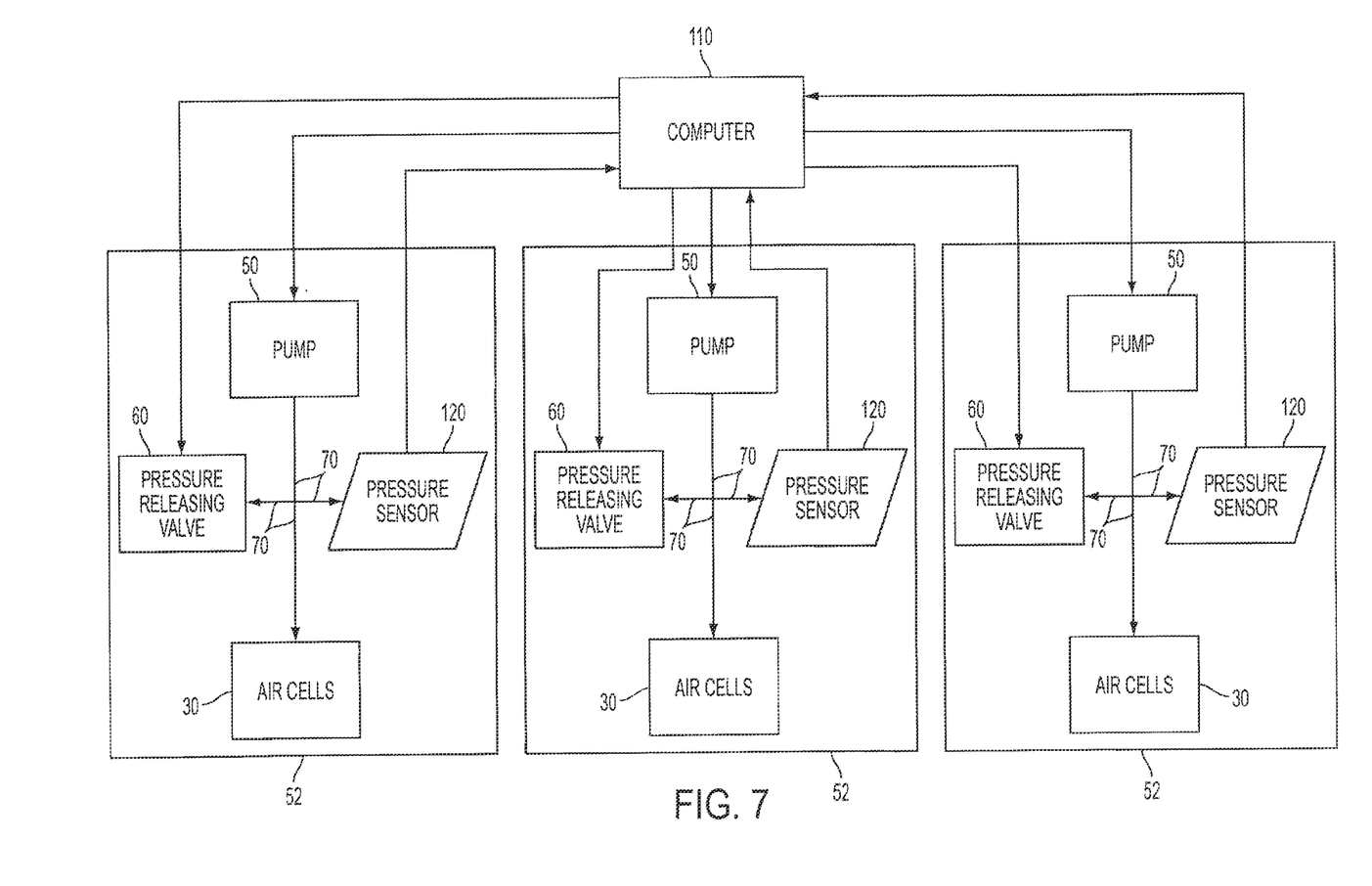
FIG. 7 is a schematic flow chart of another embodiment of the patient support system of the current application comprising a plurality of fluid pumps arranged to form a plurality of air supply subsystems.

Optionally, it is contemplated that the plurality of fluid pumps 50 can be in communication with the plurality of tubing 70 and each other by a conventional series communication arrangement. In a further aspect however, and as illustrated in FIGS. 6 and 7, the fluid pumps can be connected to different tubes of the plurality of tubing 70 to form a plurality of air supply subsystems 52. For example, in this aspect, a first fluid pump can supply air to a first air cell or to a first plurality of air cells 30, a second fluid pump can supply air to a second air cell or to a second plurality of air cells and so on, for each fluid pump provided in the air supply system 40.

In another aspect, the at least one pressure release valve 60 can be in fluid communication with the plurality of air cells 30. In one exemplary, non-limiting example, the at least one pressure release valve can be a conventional solenoid valve that is configured to be electrically coupled to a computer 110 of the control system 100. In another aspect, the at least one pressure release valve can be a conventional mechanical relief valve that is configured to selectively open at a predetermined or at an adjustable pressure. The at least one pressure release valve 60 can be configured to release air from at least a portion of the plurality of air cells and/or the plurality of tubing so that the air pressure within at least a portion of the patient support system 20 can be maintained at an appropriate, desired set point to reduce or prevent the formation of bedsores on a user of the system.

In one aspect, if there is only one fluid pump 50, or the plurality of fluid pumps are arranged in parallel fluid communication with each other, at least one pressure release valve 60 can be used to reduce pressure within the air supply system 40 and within the plurality of air cells 30 that are in sealed fluid communication with the air supply system. In another aspect, however, if a plurality of fluid pumps are arranged to form a plurality of air supply subsystems 52, as exemplified in FIG. 6, at least one pressure release valve can be used in each air supply subsystem to reduce the air pressure within the air supply subsystem and within the air cell or plurality of air cells 30 that are in sealed fluid communication with the air supply subsystem. Thus, it will be appreciated that, in one example, if there are two, three, or more air supply subsystems 52, there can be two, three or more corresponding pressure release valves, so that each air supply subsystem has at least one pressure release valve 60.

The plurality of tubing 70 can interconnect the at least one fluid pump 50, the at least one pressure release valve 60, the plurality of air cells 30, and/or at least one pressure sensor 120, placing them in sealed fluid communication with each other. The tubing can be conventional tubing made of polymeric components, metallic, and/or other materials having a cross-sectional area sized to distribute air to the plurality of air cells 30 at the proper air flow rate and pressure, as commonly known in the arts.

In another aspect, the plurality of tubing can be configured to form at least one air cell manifold 72 to more evenly distribute air to the plurality of air cells. In one aspect, the at least one air cell manifold can be attached to the at least one mounting sheet 36 with, for example and without limitation, adhesives. In another aspect, at least a portion of the at least one air cell manifold can be formed integrally with at least a portion of the at least one mounting sheet, such that at least a portion of the at least one air cell manifold is formed from at least a portion of the at least one mounting sheet 36. In still another aspect, the at least one air cell manifold 72 can be unattached to the at least one mounting sheet.

Figure 9:
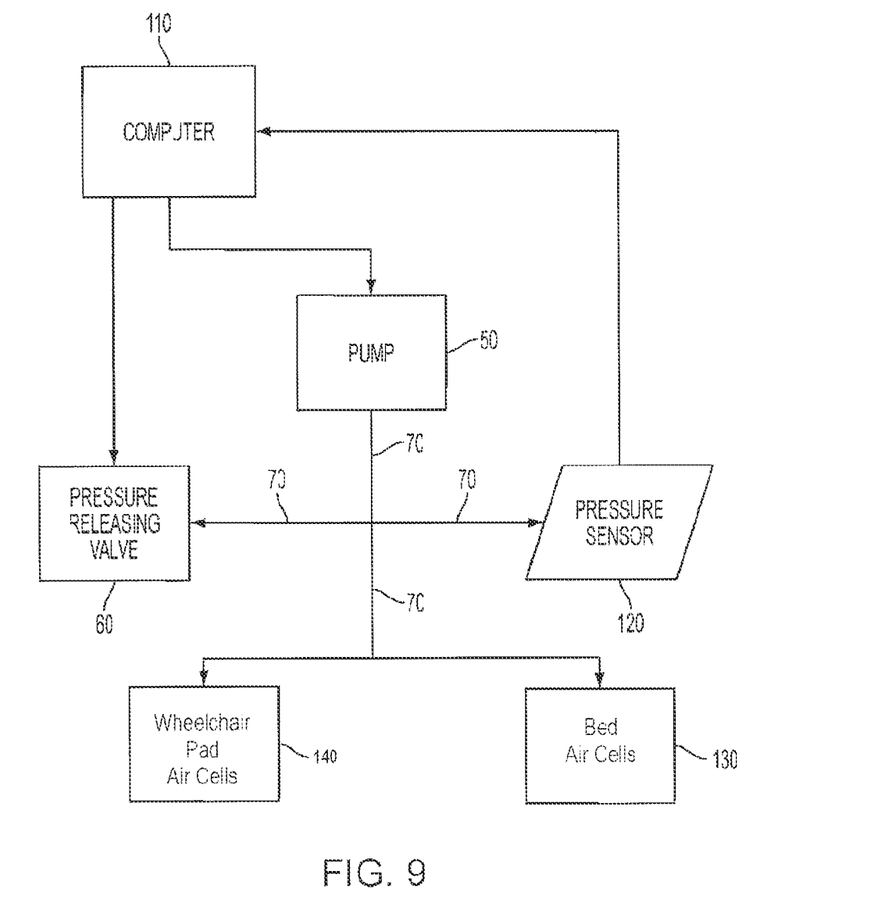
FIG. 9 is a schematic view of a patient support system, according to one aspect.

One embodiment of the patient support system is schematically illustrated in FIG. 9. In one aspect, the fluid pump 50 can have two outlet connections each in communication with the tubing 70. A first outlet connection of the fluid pump can connect the pump 50 to the air cells that form a no-air-loss or low-air-loss bed mattress 130, while a second outlet connection of the fluid pump can connect the pump 50 to a plurality of cells that form a no-air-loss patient support surface 34, in this case a no-air-loss wheelchair pad 140. In this way, a user can selectively switch the pump to control either the bed or the wheelchair pad. It is contemplated that, in one instance, the pump 50 can automatically realize when a patient is on the wheelchair pad 140 and the pressure within at least a portion of the plurality no-air-loss air cells is within a predetermined tolerance of the desired patient support system air pressure, the fluid pump can be operatively uncoupled from the air cells. For example, the fluid pump 50 can be automatically locked so that no air can go into or out of the no-air-loss cells. In another example, the user can physically disconnect the no-air-loss cells of the wheelchair pad 140 from the pump 50 so that a patient can receive continued no-air-loss support and remain in equilibrium while on the no-air-loss wheelchair pad.

As schematically illustrated in FIGS. 4-7, the control system 100 of the patient support system 20 can comprise a computer 110 that is operatively in communication with at least one pressure sensor 120. In one aspect, the at least one pressure sensor can be a conventional pressure sensor suitable for measuring the pressure of a fluid within a vessel. In one exemplary, non-limiting example, the at least one pressure sensor can be electrically coupled to the computer. In this aspect, the at least one pressure sensor can be configured to send an electrical pressure measurement signal to the computer representing the air pressure within the patient support system 20 or air supply subsystems 52 at a predetermined period of time, which is, as one will appreciate, representative of the air pressure therein the air cells. In one aspect, the at least one pressure sensor can send pressure measurement signals to the computer 110 repeatedly at selected time intervals, such as, for example and without limitation, multiple times per second. In another exemplary aspect, the at least one pressure sensor 120 can send a pressure measurement signal to the computer every second. In yet another exemplary aspect, the at least one pressure sensor can send a pressure measurement signal to the computer 110 at a greater time interval, such as, for example and without limitation, once every five seconds, once every ten seconds, once every twenty seconds, once every minute, and the like.

In one aspect, the at least one pressure sensor 120 can measure the air pressure within the air supply system. In another aspect, the at least one pressure sensor can be in sealed fluid communication with the tubing 70 of the air supply system 40. In another aspect, it is contemplated that the at least one pressure sensor can be in sealed fluid communication with the tubing at any point within the plurality of tubing. In a further aspect, the at least one pressure sensor can be in sealed fluid communication with a portion of the tubing near the at least one fluid pump 50. In another aspect, the at least one pressure sensor can be in sealed fluid communication with at least one air cell of the plurality of air cells 30.

In one aspect, if there is only one fluid pump, or a plurality of fluid pumps 50 that are arranged in a parallel fluid communication arrangement, a single pressure sensor can be used to measure the air pressure within the air supply system 40. As one skilled in the art will appreciate, if a plurality of fluid pumps are arranged to form a plurality of air supply subsystems 52, a pressure sensor can be used in each air supply subsystem to measure the air pressure within the air supply subsystem. Thus, if there are two, three, or more air supply subsystems, there can be two, three or more pressure sensors, so that each air supply subsystem has at least one pressure sensor.

In another aspect, the at least one pressure release valve 60, the at least one fluid pump 50, the computer 110, and/or the at least one pressure sensor 120 can be contained within a housing 80. In one aspect, the housing can be configured to restrict users from accessing the moving parts of the at least one pressure release valve, the at least one fluid pump and/or the at least one pressure sensor. In another aspect, the housing can be configured or insulated to reduce noise created by the moving parts of the at least one pressure release valve, the at least one fluid pump and/or the at least one pressure sensor 120.

The computer 110 can be a standard computer, as is known in the arts. In one aspect, the computer can comprise a system processor. In another aspect, a computer readable storage medium can be coupled to the processor. The processor can be coupled to a display or monitor and to a user input device, such as a keyboard, mouse, or other suitable device. The processor of the computer can also be coupled to the at least one pressure sensor 120 for inputting the pressure of the air supply system 40 or air supply subsystems 52, as measured by the at least one pressure sensor. As one will appreciate, the operation of the at least one fluid pump 50 and the at least one pressure release valve 60 can be operatively coupled to and controlled by the computer, as will be described more fully below. In another aspect, the computer readable medium can include hardware and/or software such as, by way of example only, magnetic disks, magnetic tape, optically readable medium such as CD ROM's, and semi-conductor memory such as PCMCIA cards. In each aspect, the medium can take the form of a portable item such as a small disk, floppy diskette, cassette, or it can take the form of a relatively large or immobile item such as hard disk drive, solid state memory card, or RAM coupled to the processor. It should be noted that the above listed example mediums can be used either alone or in combination.

With reference to the figures, a patient support system 20 can be assembled to comprise any or all of the components as described above. In one aspect, at least one mounting sheet 36 can be dimensioned or sized to correspond to the wheelchair surface 12 or the surface segments 13 of the desired wheelchair 10. If the wheelchair has a plurality of surface segments 13, then a plurality of mounting sheets can be dimensioned or sized to correspond to the surface segments. In one aspect, the plurality of air cells 30 can be affixed to the at least one mounting sheet 36 or formed integrally with the at least one mounting sheet, such that at least a portion of an air cell is formed from at least a portion of the at least one mounting sheet, as described above. In one aspect, the plurality of air cells can be arranged with the opening 33 of each air cell at the proximal end 31 of each air cell. In another aspect, the plurality of air cells 30 can be arranged with the opening of each air cell at the distal end of 32 each air cell. In still another aspect, the plurality of air cells can be arranged with the opening 33 of each air cell at any combination of the proximal end or distal end of each air cell. In one exemplary aspect, the location of the opening of each air cell can alternate between a proximal end of an air cell, the distal end of an adjacent air cell, and so on. It is contemplated that the opening of each air cell can be positioned anywhere as desired on the respective air cell. The plurality of air cells 30 forming a no-air-loss patient support surface 34 can be arranged to form the wheelchair pad 140 that can be positioned to overlie at least a portion of the wheelchair surface 12 or the surface segments 13 of the desired wheelchair 10.

In one aspect, the plurality of tubing 70 can be configured to form the at least one air cell manifold 72. The at least one air cell manifold can be securely attached to the opening 33 in each of the plurality of air cells 30 with conventional connectors 74, such that the tubing is placed in sealed fluid communication with the opening in each air cell of the plurality of air cells. In one aspect, the at least one air cell manifold can be securely attached to the at least one mounting sheet 36. In another aspect, however, and as described above, the at least one air cell manifold can be formed integrally with the mounting sheet, such that at least a portion of the at least one air cell manifold is formed from at least a portion of the at least one mounting sheet. In another aspect, if a plurality of mounting sheets are present, then an air cell manifold 72 can be securely attached to or formed integrally with each mounting sheet 36. In still another aspect, the at least one air cell manifold can be unattached to the at least one mounting sheet.

The plurality of tubing 70 can be securely attached to the at least one fluid pump 50, the at least one pressure release valve 60, and the at least one pressure sensor 120 with standard connectors, as known in the arts, so that the at least one fluid pump, the at least one pressure release valve, and the at least one pressure sensor are in sealed fluid communication with the plurality of tubing and each other.

Figure 5:
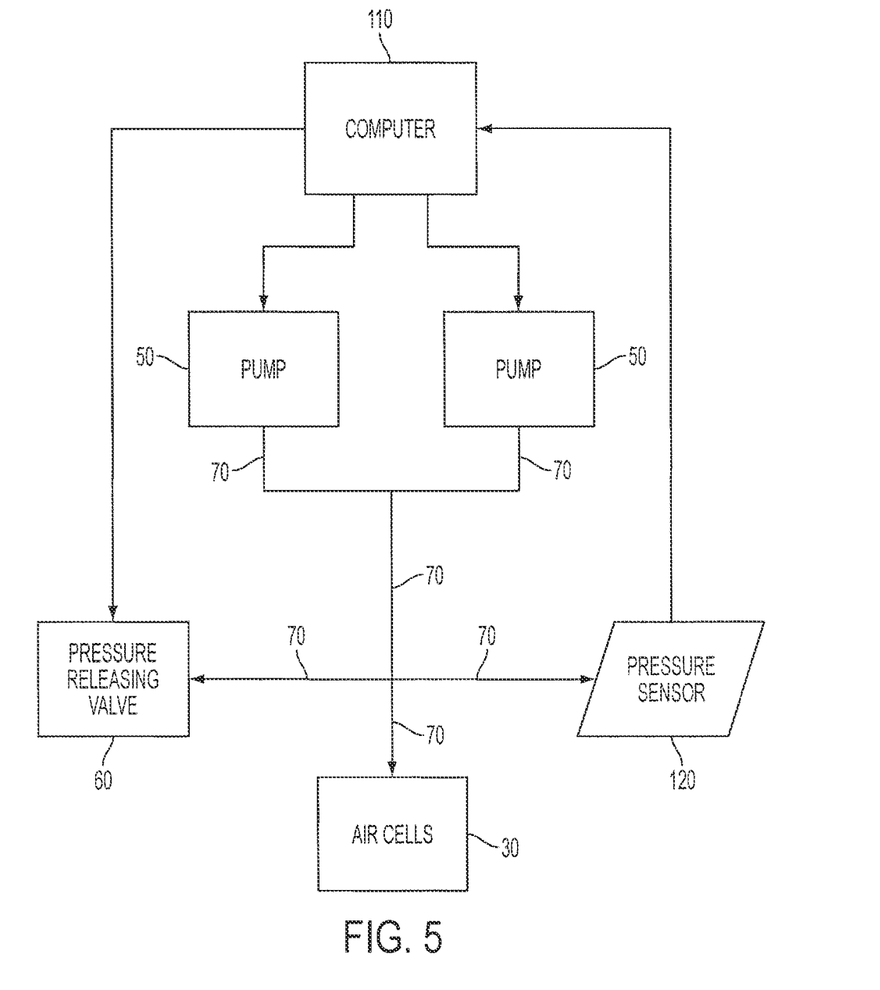
FIG. 5 is a schematic flow chart of one embodiment of the patient support system of the current application comprising a plurality of fluid pumps in serial communication with each other.

As noted above, it is contemplated that the at least one fluid pump 50 can comprise a plurality of fluid pumps. In one aspect, if the plurality of fluid pumps are interconnected in a parallel communication arrangement, as illustrated in FIG. 5, only one pressure release valve 60 and one pressure sensor 120 are required to be placed in sealed communication with the fluid pumps and the plurality of air cells 30. In another aspect, however, if the plurality of fluid pumps are arranged in separate air supply subsystems 52, as illustrated in FIGS. 6 and 7, each respective air supply subsystem can require at least one pressure release valve and at least one pressure sensor so that air pressure within the separate air supply subsystems can be controlled.

It is contemplated that each air supply subsystem 52, if present, can supply air to different air cells and/or groups of air cells of the plurality of air cells 30. In one example, a first air supply subsystem could supply air to a plurality of air cells having their opening 33 on the distal end 32 of each air cell, and a second air supply subsystem could supply air to a plurality of air cells having their opening on the proximal end 31 of each air cell. In a second example, a first air supply subsystem could supply air to every other air cell of the plurality of air cells 30, and a second air supply subsystem could supply air to the remaining air cells. In a third example, a first air supply subsystem 52 could supply air to every third air cell of the plurality of air cells, a second air supply subsystem could supply air to the next every third air cell of the plurality of air cells, and a third air supply subsystem could supply air to the remaining every third air cell of the plurality of air cells. As one of skilled in the art will appreciate, this use of a plurality of subsystems to supply air to groups of the plurality of air cells 30 can continue for any number of air supply subsystems.

In one aspect, the at least one fluid pump 50, the at least one pressure release valve 60 and the at least one pressure sensor 120 can be electrically coupled to the computer 110. Additionally, in another aspect, the at least one liquid-impermeable covering can be placed over the plurality of air cells 30 and the at least one mounting sheet 36.

In use, at least a portion of the air cells of the patient support system 20 can be positioned on the wheelchair surface 12 of the wheelchair 10 (if they are not otherwise integrated therein the wheelchair surface of the wheelchair), and the plurality of tubing 70 of the patient support system can be connected as described above, if not previously connected. If the wheelchair has a plurality of surface segments 13, each segment can have at least a portion of the air cells of the patient support system placed thereon. Optionally, in one aspect, at least one foam pad can be placed under the patient support system 20. In one aspect, it is contemplated that the at least one foam pad can be dimensioned or sized so that the patient support system can be used on any conventional wheelchair.

The computer 110 can be connected to a power source, such as a battery or a standard electrical outlet. In one aspect, a user can input the desired air pressure set point into the processor of the computer using the user input device. The at least one pressure sensor 120 can measure the air pressure within the air supply system and send a signal to the processor representing the air pressure within the respective air cells. The processor can compare the signal from the at least one pressure sensor to the desired air pressure set point. If the sensed pressure is higher than the air pressure set point, the processor can send a signal to the appropriate at least one pressure release valve 60 causing the valve to selectively open for a period of time, thus releasing air and decreasing the air pressure within the respective air cells. Conversely, if the sensed pressure is lower than the desired air pressure set point, the processor can send an actuation signal to the at least one fluid pump 50 to cause the at least one fluid pump to turn on for a period of time, thereby supplying additional air to the air cells, at least partially inflating the air cells and thereby increasing air pressure within the air cells. Thus, it is contemplated that the at least one pressure sensor, the computer, the at least one pressure release valve and the at least one fluid pump can form a feedback circuit that is configured to maintain the air pressure therein the respective air cells at approximately the desired air pressure. If a plurality of air supply subsystems 52 are present, it is also contemplated that similar feedback circuits can be formed to maintain the air pressure therein the respective air cells of the respective subsystems at approximately the desired air pressure (which can be individually set for each respective subsystem or, optionally, can be set at an uniform air pressure for all of the respective subsystems).

In one aspect, an external force can be exerted onto wheelchair pad formed by the no-air-loss patient support surface 34 on the wheelchair 10 by a patient, a physician and/or other operating room personnel and the like, placing the no-air-loss patient support surface in a loaded condition. In another aspect, the no-air-loss patient support surface 34 can be in the loaded condition before the patient support system 20 has been inflated to the desired air pressure set point. In another aspect, the patient support system can be inflated to the desired air pressure set point or set points, as described above, before an external force is applied thereto the no-air-loss patient support surface. In this aspect, after the no-air-loss patient support surface is in the loaded condition, the air pressure within the patient support system can change due to the external force. The at least one pressure sensor 100 can detect this change, and the patient support system 20 can adjust itself accordingly, also as described above, until the desired air pressure set point has been achieved.

In one aspect, once the predetermined no-air-loss patient support system air pressure set point has been achieved, within a predetermined tolerance, no more adjustments to the air pressure within the patient support system 20 are made. In another aspect, the no-air-loss patient support system can be closed once the no-air-loss surface (and thus the patient) has reached equilibrium in a loaded condition. In this aspect, after reaching equilibrium under loaded conditions, no more adjustments to the air pressure within the patient support system 20 are made (the system is closed) before moving the wheelchair, so that during wheelchair use that patient will not have to carry around a computer and battery to readjust the patient support system 20.

In one aspect, the computer 110 can continue to receive input from the at least one pressure sensor 120 for monitoring purposes, for example. This information can be saved to the computer readable storage medium for later retrieval or viewing on the display or monitor. In this aspect, however, once the desired set point has been reached, the computer will not send a signal to the at least one fluid pump 50 and/or to the at least one pressure release valve 60. Because the plurality of air cells 30 are no-air-loss air cells, once the desired air pressure set point within the patient support system has been achieved within a predetermined tolerance and with a patient on the no-air-loss patient support surface 34, it is contemplated that no additional changes to the air pressure within the system will be required because the air pressure within the system will remain constant. In this aspect, any extra load or pressure placed on the system at this point will therefore cause no adjustments to be made to the air pressure with the system from the computer control circuit.

In another aspect, once the desired no-air-loss patient support system air pressure set point has been reached, within a predetermined tolerance, the computer 110 can turn off automatically. In one aspect, for example, if the sensed no-air-loss patient support system air pressure has not changed for a predetermined period of time, the computer can automatically turn off so that no additional changes to the air pressure within the system will be made. In another aspect, the predetermined period of time can be, for example and without limitation, 10 seconds, 20 seconds, 30 seconds, 40 seconds, 50 seconds, 1 minute, 2 minutes, 3 minutes, 4 minutes, 5 minutes, 10 minutes, 15 minutes, and the like. In still another aspect, once the desired no-air-loss patient support system air pressure set point has been reached, within a predetermined tolerance, the computer 110 can be turned off manually by a user, so that no additional changes to the air pressure within the system will be made. In yet another aspect, once the desired no-air-loss patient support system air pressure set point has been reached, within a predetermined tolerance, the at least one fluid pump and the at least one pressure release valve can be uncoupled from the portion of the plurality no-air-loss air cells that are within a predetermined tolerance of the desired patient support system air pressure. With the patient support system at a desired pressure, the patient can leave the computer attached to the bed frame and the low-air-loss or no-air-loss support mattress while moving the no-air-loss wheelchair pad on the wheelchair.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A wheelchair patient support system for reducing the formation of bedsores on a patient positioned on a wheelchair, the system comprising:
    a plurality of no-air-loss air cells, wherein at least a portion of the plurality of no-air-loss air cells are configured to engage the wheelchair, and wherein at least a portion of the plurality of no-air-loss air cells form a no-air-loss patient support surface;
    at least one fluid pump coupled to the plurality of no-air-loss air cells;
    at least one pressure release valve coupled to the plurality of no-air-loss air cells;
    at least one pressure sensor coupled to the plurality of no-air-loss air cells;
    a computer having a processor, wherein the computer is coupled to the at least one fluid pump, the at least one pressure release valve and the at least one pressure sensor,
    wherein the at least one pressure sensor is configured to send a pressure signal to the computer representing the air pressure within at least a portion of the plurality of no-air-loss air cells, wherein the computer is configured to:
        activate at least one of the at least one fluid pump and the at least one pressure release valve if the sensed air pressure differs from a desired air pressure set point; and
        close the patient support system when the sensed air pressure within at least a portion of the plurality of no-air-loss air cells is within a predetermined tolerance of the desired air pressure set point in a loaded condition,
    wherein, when the patient support system in closed, no adjustments to the air pressure within the plurality no-air-loss air cells are subsequently made.

2. A wheelchair patient support system for reducing the formation of bedsores on a patient positioned on a wheelchair, the system comprising:
    a plurality of no-air-loss air cells, wherein at least a portion of the plurality of no-air-loss air cells are configured to engage the wheelchair, and wherein at least a portion of the plurality of no-air-loss air cells form a no-air-loss patient support surface;
    a means for supplying air to and removing air from the plurality of no-air-loss air cells comprising at least one fluid pump, at least one pressure release valve, and a plurality of tubing, wherein the means for supplying air to and removing air from the plurality of no-air-loss air cells is operably connected to the plurality of no-air-loss air cells;
    a processor coupled to the means for supplying air to and removing air from the plurality of no-air-loss air cells; and
    at least one pressure sensor coupled to the processor, wherein the at least one pressure sensor senses the air pressure within the plurality of no-air-loss air cells and wherein the at least one pressure sensor sends a signal to the processor representing the air pressure within the respective air cells,
    wherein the processor s configured to:
        activate the means for supplying air to and removing air from the plurality of no-air-loss air cells if the sensed air pressure differs from a desired air pressure set point; and
        close the patient support system when the sensed air pressure within at least a portion of the plurality of no-air-loss air cells is within a predetermined tolerance of the desired air pressure set point in a loaded condition,
    wherein, when the patient support system in closed, no adjustments to the air pressure within the plurality no-air-loss air cells are subsequently made, and wherein the processor continues to receive the sensed air pressure within the plurality of no-air-loss air cells when the system is closed.

3. The wheelchair patient support system of claim 2, wherein the means for supplying air to and removing air from the plurality of no-air-loss cells can be selectively switched from a no-air-loss bed and the no-air-loss air cells of the wheelchair patient support system.

4. The wheelchair patient support system of claim 2, wherein the means for supplying air to and removing air from the plurality of no-air-loss cells can be selectively switched from a low-air-loss bed and the no-air-loss air cells of the wheelchair patient support system.

5. The wheelchair patient support system of claim 2, wherein at least a portion of the no-air-loss air cells are at least partially inflated by the at least one fluid pump to a desired patient support system air pressure.

6. The wheelchair patient support system of claim 5, further comprising a means for identifying the air pressure within the plurality of no-air-loss cells.

7. The wheelchair patient support system of claim 2, wherein the computer is programmed to close the patient support system upon operator election.

8. The wheelchair patient support system of claim 2, wherein the means for operatively uncoupling the plurality of no-air-loss cells from the at least one fluid pump comprises a signal for signaling a user to disconnect the at least one fluid pump from the plurality of no-air-loss cells.

9. The wheelchair patient support system of claim 2, wherein each no-air-loss cell of the plurality of no-air-loss cells defines an opening in fluid communication with the at least one fluid pump and the at least one pressure release valve.

10. The wheelchair patient support system of claim 9, wherein the opening in each no-air-loss cell of the plurality of no-air-loss cells is located in a distal end of the no-air-loss cell.

11. The wheelchair patient support system of claim 2, further comprising at least one liquid-impermeable covering configured to cover at least a portion of the plurality of no-air-loss air cells.

12. The wheelchair patient support system of claim 2, wherein the at least one pressure sensor is interposed therebetween the at least one fluid pump and the plurality of no-air-loss air cells.

13. The wheelchair patient support system of claim 2, wherein the at least one fluid pump comprises a plurality of fluid pumps, and wherein the at least one pressure release valve comprises a plurality of pressure release valves.

14. The wheelchair patient support system of claim 13, further comprising a plurality of air supply subsystems, wherein each air supply subsystem comprises at least one fluid pump of the plurality of fluid pumps in fluid communication with at least one no-air-loss air cell of the plurality of no-air-loss air cells.

15. The wheelchair patient support system of claim 14, wherein each air supply subsystem further comprises at least one pressure release valve.

16. The wheelchair patient support system of claim 2, wherein the at least one pressure sensor is coupled to the computer and is configured to send a signal to the computer representing the air pressure within at least a portion of the patient support system.

17. The wheelchair patient support system of claim 16, wherein the computer is configured to:
compare the signal representing the air pressure within at least a portion of the patient support system to the desired patient support system air pressure; and
determine whether to activate the means for supplying air to and removing air from the plurality of no-air-loss air cells in order to adjust the air pressure within at least a portion of the patient support system to within a predetermined tolerance of the desired patient support system air pressure.

18. The wheelchair patient support system of claim 17, wherein, when the no-air- loss patient support surface is in a loaded condition in which an external force is applied to the no-air-loss patient support surface, and when the air pressure within at least a portion of the plurality no-air-loss air cells is within a predetermined tolerance of the desired patient support system air pressure, the patient support system is closed and the at least one fluid pump and the at least one pressure release valve are operatively uncoupled from the portion of the plurality no-air-loss air cells that are within a predetermined tolerance of the desired patient support system air pressure.

19. The wheelchair patient support system of claim 2, wherein the at least one pressure sensor is coupled to the computer and sends a signal to the computer representing the air pressure within at least one no-air-loss air cell of the plurality of no-air-loss air cells.

20. The wheelchair patient support system of claim 2, wherein at least a portion of the plurality of no-air-loss cells are configured to engage the wheelchair laterally.

21. The wheelchair patient support system of claim 2, wherein the plurality of tubing is configured to form at least one air cell manifold in fluid communication with at least one no-air-loss air cell of the plurality of no-air-loss air cells.

22. The wheelchair patient support system of claim 2, wherein, after the patient support system is closed, the computer is configured to turn off if the sensed air pressure has not changed for a predetermined period of time.

23. The wheelchair patient support system of claim 2, wherein the computer is configured to continue to receive the pressure signal after the patient support system is closed and to save the sensed air pressure data to a computer readable storage medium.

24. The wheelchair patient support system of claim 23, wherein, after the patient support system is closed, the computer is configured to turn off if the sensed air pressure has not changed for a predetermined period of time.

25. A method for reducing the formation of bedsores on a patient positioned on a wheelchair, the method comprising:
providing a plurality of no-air-loss air cells, wherein the plurality of no-air-loss cells are configured to engage the wheelchair, and wherein at least a portion of the plurality of no-air-loss air cells form a no-air-loss patient support surface;
sensing the air pressure within at least a portion of the plurality of no-air-loss air cells;
controlling the supply of air to and removal of air from the plurality of no-air-loss air cells until a desired air pressure set point is obtained therein at least a portion of the plurality of no-air-loss air cells to within a predetermined tolerance;
activating the supply of air to and removal of air from the plurality of no-air-loss air cells if the sensed air pressure differs from the desired air pressure set point; and
closing the patient support system when the sensed air pressure within at least a portion of the plurality of no-air-loss air cells is within a predetermined tolerance of the desired air pressure set point in a loaded condition, wherein, when the patient support system in closed, no adjustments to the air pressure within the plurality no-air-loss air cells are subsequently made, and wherein the computer continues to receive input from the at least one pressure sensor for monitoring purposes when the system is closed.

26. The method of claim 25, wherein the step of controlling the supply of air to and removal of air from the plurality of no-air-loss air cells until a desired air pressure is obtained comprises:
comparing the air pressure therein at least a portion of the plurality of no-air-loss air cells to the desired air pressure set point;
releasing air from the respective no-air-loss air cells if the air pressure therein the respective no-air-loss air cells is higher than the desired air pressure set point;
supplying air to the respective no-air-loss air cells if the air pressure therein the respective no-air-loss air cells is lower than the desired air pressure set point;
closing the system when the air pressure is in a specified range of the desired set point; and
identifying to the user that the air pressure is in the specified range.

27. A patient support system for reducing the formation of bedsores on a patient positioned on a wheelchair, the system comprising:
a plurality of no-air-loss air cells, wherein at least a portion of the plurality of no-air-loss cells are configured to engage the wheelchair, and wherein at least a portion of the plurality of no-air-loss air cells form a no-air-loss patient support surface;
at least one fluid pump coupled to the plurality of no-air-loss air cells;
at least one pressure release valve coupled to the plurality of no-air-loss air cells;
at least one pressure sensor coupled to the plurality of no-air-loss air cells; and
a computer having a processor, wherein the computer is coupled to the at least one fluid pump, the at least one pressure release valve and the at least one pressure sensor, wherein the at least one pressure sensor is configured to send a signal to the computer representing the air pressure within at least a portion of the plurality of no-air-loss air cells, wherein a mode of operation of the computer is selectable between a) a first mode of operation, in which the computer is configured to actuate at least one of the at least one fluid pump and the at least one pressure release valve in order to adjust the air pressure within at least a portion of the plurality of no-air-loss air cells to within a predetermined tolerance of a desired patient support system air pressure, and, in a loaded condition in which an external force is applied to at least a portion of the plurality of no-air-loss air cells, b) a second mode of operation, in which the computer is configured to close the patient support system when the at least one pressure sensor senses an air pressure within at least a portion of the plurality of no-air-loss air cells that is within a predetermined tolerance of a desired patient support system air pressure wherein, in a loaded condition in which an external force is applied to at least a portion of the plurality of no-air-loss air cells, and wherein, when the patient support system in closed, no adjustments to the air pressure within the plurality no-air-loss air cells are subsequently made.

* * * * *